(12) United States Patent
Fey

(10) Patent No.: US 10,408,785 B2
(45) Date of Patent: Sep. 10, 2019

(54) METHOD AND DEVICE FOR DETERMINING AN INTERNAL RESISTANCE OF A SENSOR ELEMENT

(71) Applicant: Robert Bosch GmbH, Stuttgart (DE)

(72) Inventor: Michael Fey, Wiernsheim (DE)

(73) Assignee: Robert Bosch GmbH, Stuttgart (DE)

( * ) Notice: Subject to any disclaimer, the term of this patent is extended or adjusted under 35 U.S.C. 154(b) by 96 days.

(21) Appl. No.: 15/565,254

(22) PCT Filed: Apr. 6, 2016

(86) PCT No.: PCT/EP2016/057536
§ 371 (c)(1),
(2) Date: Oct. 9, 2017

(87) PCT Pub. No.: WO2016/173814
PCT Pub. Date: Nov. 3, 2016

(65) Prior Publication Data
US 2018/0059045 A1   Mar. 1, 2018

(30) Foreign Application Priority Data

Apr. 29, 2015 (DE) .......... 10 2015 207 880

(51) Int. Cl.
*G01N 27/40* (2006.01)
*G01N 27/406* (2006.01)
(Continued)

(52) U.S. Cl.
CPC ..... *G01N 27/4065* (2013.01); *G01N 27/4073* (2013.01); *G01N 27/4175* (2013.01)

(58) Field of Classification Search
CPC ........... G01N 27/4065; G01N 27/4073; G01N 27/4175
See application file for complete search history.

(56) References Cited

U.S. PATENT DOCUMENTS

| 6,397,659 | B1* | 6/2002 | Mizoguchi | G01N 27/407 |
|---|---|---|---|---|
| | | | | 73/23.2 |
| 2009/0051373 | A1* | 2/2009 | Kato | G01N 27/4065 |
| | | | | 324/693 |

(Continued)

FOREIGN PATENT DOCUMENTS

| DE | 102008042268 A1 | 4/2010 |
|---|---|---|
| DE | 112008001147 T5 | 4/2010 |
| DE | 102011089383 A1 | 6/2013 |

OTHER PUBLICATIONS

Fischer et al., "Detection of NO by pulsed polarization of Pt I YSZ", Solid State Ionics, vol. 262, Jan. 31, 2014, pp. 288-291.
(Continued)

*Primary Examiner* — Jeff W Natalini
(74) *Attorney, Agent, or Firm* — Norton Rose Fulbright US LLP; Gerard Messina

(57) ABSTRACT

A method for determining an internal resistance of a sensor element. The method includes: a) applying a current pulse to the sensor element; the current pulse inducing a charge transfer in the sensor element; the occurrence of the charge transfer causing an increase in the electrical voltage between the first electrode and the second electrode of the sensor element; b) ascertaining a value for the increase in the electrical voltage between the first electrode and the second electrode, step b) being performed at least twice at different points in time during the occurrence of the charge transfer; and a value for increasing the electrical voltage being ascertained therefrom at various points in time; and c) determining the internal resistance of the sensor element from the values for increasing the electrical voltage that are ascertained at different points in time during the occurrence of the charge transfer.

10 Claims, 2 Drawing Sheets

(51) Int. Cl.
*G01N 27/407* (2006.01)
*G01N 27/417* (2006.01)

(56) References Cited

U.S. PATENT DOCUMENTS

| | | | | |
|---|---|---|---|---|
| 2009/0308135 A1* | 12/2009 | Reinshagen | ........... | G01K 7/183 |
| | | | | 73/23.2 |
| 2010/0073017 A1* | 3/2010 | Bevot | ................ | G01N 27/4065 |
| | | | | 324/703 |
| 2015/0171455 A1* | 6/2015 | Mills | ..................... | H01M 8/144 |
| | | | | 429/422 |
| 2015/0293053 A1* | 10/2015 | Akiyama | ............. | G01N 27/419 |
| | | | | 204/408 |

OTHER PUBLICATIONS

Reif, Sensoren im Kraftfahrzeug [Sensors in the Motor Vehicle], 2nd edition, 2012, pp. 160-165.
International Search Report dated Jun. 9, 2016 of the corresponding International Application PCT/EP2016/057536 filed Apr. 6, 2016.

\* cited by examiner

METHOD AND DEVICE FOR DETERMINING AN INTERNAL RESISTANCE OF A SENSOR ELEMENT

FIELD

The present invention relates to a method and a device for determining an internal resistance of a sensor element that is adapted for ascertaining at least one proportion of a measuring gas component having bound oxygen in a gas mixture in a measuring gas chamber, in particular in an exhaust gas of an internal combustion engine. The present invention also relates to a computer program that is adapted for performing the steps of the mentioned method, to an electronic storage medium upon which such a computer program is stored, and an electronic control unit that includes such an electronic storage medium.

BACKGROUND INFORMATION

Sensor elements for ascertaining at least one proportion of a gas in a gas mixture are known from the related art. Without limiting other possible embodiments, the present invention is described in the following with reference to devices used for quantitatively and/or qualitatively ascertaining at least one proportion, in particular of a partial pressure and/or a volume fraction and/or a mass fraction of a gas in a gas mixture. The gas may be an exhaust gas of an internal combustion engine, for example, in particular in automotive applications.

Most notably, a lambda probe is used as sensor element for ascertaining the gas proportion. Lambda probes are described, for example, in Konrad Reif (publisher): *Sensoren im Kraftfahrzeug* (Sensors in the Motor Vehicle), 2nd edition, 2012, pp. 160-165. Different variants of lambda probes are known from the related art.

These include lambda probes having a cell that are also referred to as "two-point lambda probes." The two-point lambda probes compare the residual oxygen proportion in the exhaust gas to the oxygen proportion of a reference gas atmosphere that can be present as circulating air inside of the sensor device, and indicate whether there is a rich mixture (i.e., lambda<1) or a lean mixture (i.e., lambda>1) in the exhaust gas. In the lambda probe that includes a cell, an external electrode is in contact with a gas chamber having a high oxygen concentration, preferably a reference volume. A fixed voltage is applied between the external electrode and an internal electrode of the cell. As soon as an oxygen concentration in a cavity approaches 0, a Nernst potential rises sharply and partially compensates for the applied voltage. This makes it possible to adjust and maintain a constant oxygen concentration in the cavity with a high degree of accuracy.

For various reasons, it may be advantageous to know the internal resistance of the sensor element, particularly since the internal resistance of the sensor element influences different properties of the sensor element and/or an engine management system that accesses quantities measured by the sensor element. To be mentioned by way of example in this context are electrical diagnoses of the sensor element, recognizing an operational readiness of the sensor element, and stabilizing the temperature of the sensor element.

To determine the internal resistance of the sensor element, it is conventionally provided that a current pulse be applied to the sensor element. In this case, the "current pulse," also referred to as a "measuring pulse," is understood, in particular, to be a sharp rise in the current that flows through the first electrode, the solid electrolyte connecting the first electrode and the second electrode, and through the second electrode of the sensor element. A resultant current loading of the sensor element brings about a charge transfer in the sensor element; the charge transfer in the sensor element being able to induce an increase in an electrical voltage present between the first electrode and the second electrode. A value for increasing the electrical voltage in response to the application of the current pulse to the sensor element can be ascertained from the observed variation of the electrical voltage between the first electrode and the second electrode immediately thereafter.

Conventionally, the internal resistance of the sensor element can be determined in each particular case by correlating the voltage between the first electrode and the second electrode of the sensor element with the described current loading to without the described current loading. However, applying the current pulse to the sensor element also leads to the above described charge transfer being induced in the sensor element. Since the cell in the sensor element also always has a capacitive portion, the current pulse can thus lead to an additional increase in the voltage present at the cell. This is known to one skilled in the art from a charging or discharging of a capacitor. However, this additional increase in voltage in the cell can lead to a deviation between the value defined for the internal resistance of the sensor element and the actual value for the internal resistance of the sensor.

For this reason, it is advantageous to record the characteristic of the electrical voltage between the first electrode and the second electrode of the sensor element under current loading preferably shortly after the current load is applied to the sensor element. In practice, however, it is not possible to implement this advantageous procedure since the sensor element, in particular the lambda probe, is typically connected via a low-pass filter to the corresponding engine management system, especially to largely suppress a transmission of high frequency signal interference from the engine management system to the sensor element. Therefore, in practice, the electrical voltage present between the first electrode and the second electrode under current loading is typically recorded only three milliseconds after the current loading begins. Although the charge transfer in the sensor element that occurs during these three milliseconds can influence the result obtained upon determining the internal resistance of the sensor element, this effect is conventionally ignored when the internal resistance is ascertained.

SUMMARY

A method and a device are, therefore, provided for determining an internal resistance of a sensor element that will at least substantially overcome the disadvantages of the conventional methods and devices.

The sensor element includes at least one cell, the cell having at least one first electrode, at least one second electrode, and at least one solid electrolyte connecting them. The two electrodes are preferably fabricated of zirconium dioxide. In a preferred embodiment, the first electrode is connected via a porous protective layer to the measuring gas chamber, while the second electrode is disposed in an electrode cavity which receives gas from the measuring gas chamber via at least one diffusion barrier. As described at the outset, a fixed voltage is applied between the first electrode and the second electrode of the cell. In response to an oxygen concentration in the electrode cavity approaching 0, a Nernst potential rises sharply and partially compensates for the applied voltage. This makes it possible to adjust and maintain a constant oxygen concentration in the electrode cavity with a high level of precision.

Thus, a first aspect of the present invention relates to a method for determining the internal resistance of the sensor element. This method includes method steps a) through c) that may preferably be implemented in the sequence shown, beginning with step a) and ending with step c). In part, however, it is likewise possible here to implement the individual steps simultaneously as well. Moreover, steps a) and b) must be performed at least twice before step c), as will be described in greater detail below.

In accordance with step a), a current pulse is applied to the present sensor element. As already described at the outset, the term "current pulse" or "measuring pulse" refers to a sharp rise in the value of the current being applied to the cell beyond the usual amount prior to the application of the current pulse and after the end thereof. Thus, the current pulse in accordance with step a) is always to be considered as an additional supplying of charges into the cell over the duration thereof. Therefore, the current pulse induces a charge transfer in the sensor element. As is known to one skilled in the art, the electrical voltage between the first electrode and the second electrode of the cell increases in response to the charge transfer being induced in the sensor element. The thereby increased value of the electrical voltage between the first electrode of the cell is ascertained in accordance with step b) of the present method.

However, in contrast to the related art methods for determining the internal resistance of the sensor element, it is provided here to perform the described step b) at least twice, preferably twice or three times, in series, in each instance, at different points in time during the occurrence of the charge transfer, and, in each case, to determine therefrom a value for the increase in the electrical voltage. In accordance with step c), the internal resistance of the sensor element is able to be determined at this point from the values for increasing the electrical voltage determined at the at least two different instants during the occurrence of the charge transfer.

Since the current pulse acting on the cell of the sensor element during step a) initially induces a build-up of the charge transfer in the sensor element and, following the end thereof, then effects a reduction in the previously generated charge transfer, it is especially advantageous to set the various points in time for determining the value for increasing the electrical voltage in the cell either only during the time period of building up the charge transfer or during the time period of reducing the same. This makes it possible to ensure that the same physical effect that influences the internal resistance of the sensor element is allowed for.

It is especially advantageous that the at least two-time recording of the value for increasing the electrical voltage in the cell may be used to determine therefrom a polarization-induced portion of the increase in the electrical voltage in the cell. The polarization-induced portion is derived during the current loading of the sensor element from the additional voltage increase described above, analogously to a charging or discharging curve of a capacitor. By determining the polarization-induced portion of the increase in the electrical voltage during the current loading, it may become possible to subtract the polarization-induced portion from a total value of the increase in the electrical voltage that is ascertained in accordance with step b) in order to thereby determine merely an ohmic portion of the increase in the electrical voltage in the cell. Using this ohmic portion of the increase in the electrical voltage in the cell makes it possible to more precisely determine the ohmic internal resistance of the sensor element. At the same time, a definition of the term "internal resistance" of the sensor is also derived therefrom that may be considered as an ohmic value for a voltage present in the sensor element in response to a current being applied thereto, it being possible to disregard other effects influencing the voltage of the sensor element, in particular a likewise thereby induced polarization of the sensor element.

In particular, a time constant that describes a characteristic of the occurrence of the charge transfer in the sensor element may be determined from the values for increasing the electrical voltage in the cell that are ascertained at the different points in time during the occurrence of the charge transfer. The term "time constant" is understood to be a characteristic quantity relating to a possible polarization of the sensor element that, analogously to the known charging of a capacitor, represents the product of the value of the electrical resistance and the value of the capacitance of the capacitor if a series connection is present between the capacitor and an electrical resistance. Therefore, the polarization-induced portion of the increase in the voltage in the cell during the current loading is able to be approximated from the preferably exponential time characteristic. Consequently, as described above, the value ascertained in this manner for the polarization-induced portion of the increase in the electrical voltage in the cell may be used for more accurately determining the value for the internal resistance of the sensor element.

It is particularly advantageous here to determine the at least one time constant for the occurrence of the charge transfer in the sensor element during a time period during which it is possible to rule out or disregard any influence other factors have on the electrical voltage in the cell. Therefore, the internal resistance of the sensor element should preferably be determined in the time period during which a preferably constant lambda value prevails.

Since, at a certain temperature of the sensor element, the value observable here for the polarization of the cell typically remains constant, it may be assumed that the value of the internal resistance of the sensor element does not change for two successive measurements of the internal resistance of the sensor element taken at the same temperature thereof in accordance with the provided method. Therefore, this observation may be used, on the one hand, to possibly eliminate implausible measured values, and, on the other hand, to enhance an accuracy of the determination of the time constants by averaging results from a plurality of individual determinations of the internal resistance of the sensor element in accordance with step c).

Similarly, at least one earlier ascertained time constant may be used for a later determination of the internal resistance of the sensor element. For each individual determination, it is thereby no longer necessary to ascertain once again the time constant described above. Instead, it may be advantageous to approximate the polarization-induced portion of the increase in the electrical voltage in the cell also using a time constant determined in an earlier measurement. To this end, it may be provided to store at least one ascertained time constant in an electronic storage medium that may be advantageously configured in the engine management system. This makes it possible to ascertain the internal resistance of the sensor element at a later point in time as well without having to redetermine the time constant.

In a preferred embodiment, a duration of the current pulse applied to the sensor element is adjusted to exceed the length of the time constant determined for the occurrence of the charge transfer in the sensor element. For this reason, it may be practical to activate the current loading of the sensor element once or at specific intervals over a relatively long period of time, particularly when the value for the time constant exceeds the otherwise customary duration of the current loading of the cell. Since this makes it possible to increase the polarization in the cell, it may be especially advantageous, as described in the German Patent Application No DE 10 2012 200 038 A1, to prolong a subsequent current loading in the opposite direction, which may also be referred to as "counter pulse," in order to altogether thereby quickly reduce the polarization in the cell of the sensor element once the described current pulse sequence has ended.

As described above, the sensor element may be connected via a low-pass filter to a control unit, in particular an engine management system. As already mentioned in this connection, the low-pass filter likewise has a corresponding time constant that one skilled in the art is able to readily derive from the correspondingly ascertained electrical quantities. Therefore, from an observation that a transient response of the voltage being applied to the cell is usually significantly longer, i.e., typically a plurality of milliseconds, than the time constant of the low-pass filter that is typically within the range from 0.1 to 0.5 milliseconds, as a result of the charge transfer induced by the current loading of the sensor element, it may be inferred that it is advantageous to select the various points in time for determining the value for increasing the electrical voltage in the cell during the build-up or reduction of the polarization in a way that makes it possible to substantially disregard any influence the low-pass filter has on the measured value. To this end, it may be provided, in particular, that the first point in time for ascertaining the value for increasing the electrical voltage in the cell is implemented in accordance with step b) once the time constant of the low-pass filter has elapsed at least three times, preferably at least five times following the beginning or ending of the current loading.

Another aspect of the present invention includes a computer program that is adapted for implementing the steps of the described method.

Another aspect of the present invention relates to an electronic storage medium that is adapted for storing a computer program equipped in this manner. In a preferred embodiment, the electronic storage medium is adapted in particular for storing at least one value, which is determined in accordance with the above described method, for a time constant for an occurrence of a charge transfer in a sensor element. Here, this ascertained value may be advantageously used for a later application of the time constant in the method without the value having to be re-determined for the time constant.

Another aspect of the present invention relates to a control unit, in particular an engine management system that is adapted to include an electronic storage medium upon which a computer program is preferably stored that is adapted for implementing the steps of the described method and possibly for also storing further values, in particular at least one time constant for an occurrence of a charge transfer in the sensor element.

Yet another aspect of the present invention relates to a device for ascertaining a proportion of a gas component from a gas mixture in a measuring gas chamber, the device having a sensor element as described above that includes at least one cell, the cell having at least one first electrode, at least one second electrode, and at least one solid electrolyte connecting them. Moreover, the device includes the control unit likewise described above, in particular an engine management system. In this connection, it is possible that the device be in a one-piece form and, preferably, in a multipiece form, in particular by configuring the sensor element as a separate element that is in two-way contact via suitable electrical connections with the control unit that is likewise formed as a separate unit.

The method in accordance with the present invention, a device adapted for carrying out the method, may make it possible to determine the internal resistance of the sensor element, in particular of the lambda probe with a greater accuracy. Thus, functions and effects, that are based on the internal resistance of the sensor element, may also be determined with greater accuracy. In particular, the temperature of the sensor element may thereby be adjusted more precisely. On the one hand, this enhances the accuracy of the signal supplied by the sensor element, and, on the other hand, diminishes any risk of damage to the sensor element caused by a possible overheating, whereby the service life of the sensor element is able to be advantageously prolonged.

The present method may be used here, in particular, in different types of sensor elements, in particular in various types of lambda probes, preferably two-point lambda probes. There are also no restrictions with regard to the control unit to be selected for the sensor element or with regard to a motor vehicle to be equipped therewith.

BRIEF DESCRIPTION OF THE DRAWINGS

Preferred exemplary embodiments of the present invention are illustrated in the figures and explained in greater detail below.

DETAILED DESCRIPTION OF EXAMPLE EMBODIMENTS

The method according to the present invention for determining an internal resistance of a sensor element is described exemplarily in the following with reference to a sensor element that is adapted for ascertaining a proportion of oxygen in an exhaust gas of an internal combustion engine, in particular with reference to a lambda probe having a cell.

Figure 1:
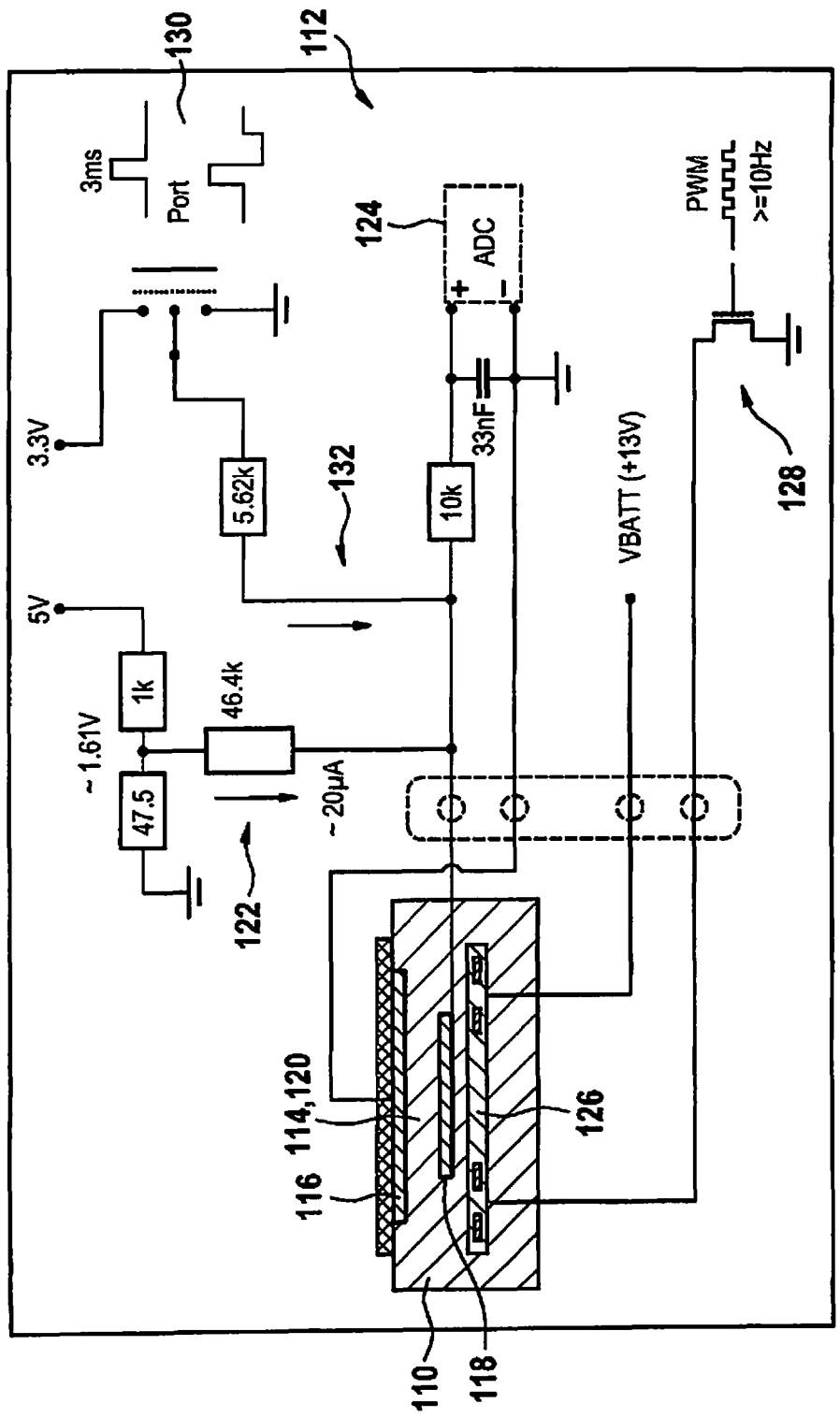
FIG. 1 shows a schematic representation of electrical circuit interconnections of a sensor element, whose internal resistance may be determined by the present invention.

FIG. 1 schematically shows a sensor element 110 for ascertaining a proportion of a gas component from a gas mixture in a measuring gas chamber, as well as corresponding electrical circuit interconnections 112. Sensor element 110 shown here exemplarily has a cell 114 that includes a first electrode 116, a second electrode 118, and a solid electrolyte 120 connecting them. Applying a current 122 to cell 114 makes it possible to determine an electrical voltage 124 between first electrode 116 and second electrode 118 using a suitable voltage detection device. Moreover, sensor element 110 shown here has a heating element 126 that may be operated by a corresponding heating control 128 to adjust the temperature of sensor element 110.

In accordance with step a) of the method for determining the internal resistance of sensor element 110, sensor element 110 has a current pulse 130 applied thereto that is supplied by a pulse generation unit 132 adapted for this purpose and is transmitted to cell 114 in addition to current 122. In response to the application of current pulse 130 to sensor element 110, a charge transfer is induced in sensor element 110 that is manifested in a measurable increase in electrical voltage 124 in cell 114 between first electrode 116 and second electrode 118.

In each instance, a value for increasing electrical voltage 124 in cell 114 between first electrode 116 and second electrode 118 is ascertained in accordance with step b) at least twice at different points in time during the occurrence of the charge transfer. The internal resistance of sensor element 110 may be determined therefrom in accordance with step c), as is more readily discernible from subsequent FIG. 2.

Figure 2:
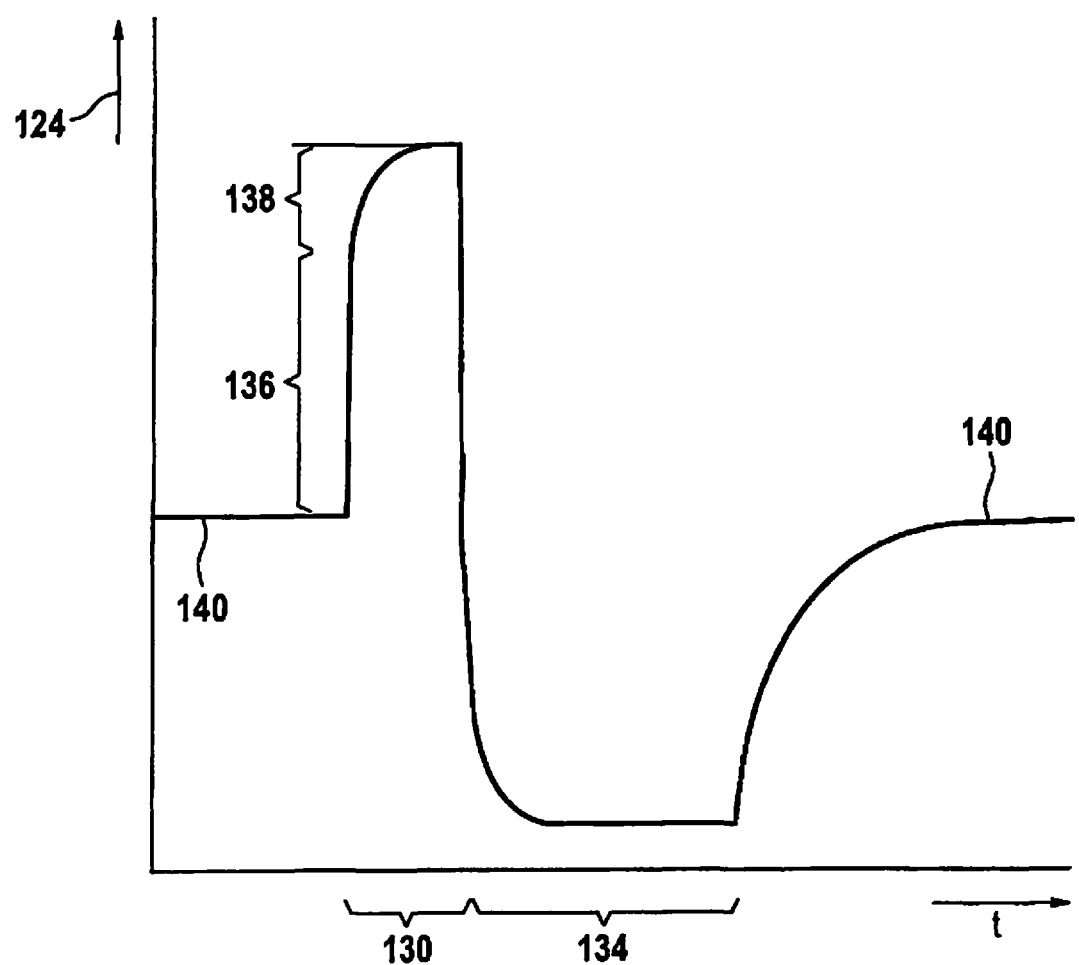
FIG. 2 schematically represents the time characteristic of the electrical voltage between the first and second electrode of the sensor element.

FIG. 2 schematically illustrates the time characteristic of electrical voltage 124 in cell 114 between first electrode 116 and second electrode 118 of sensor element 110. Here, a current pulse 130 and, subsequently, a counter pulse 134 were applied to sensor element 110. Therefore, counter pulse 134 was preferably applied to sensor element 110 to eliminate as readily as possible the polarization of sensor element 110, in particular of cell 114 caused by the application of current pulse 130 to sensor element 110.

The time characteristic of electrical voltage 124 of cell 114 illustrated in FIG. 2 includes both an ohmic portion 136, as well as a polarization-induced portion 138 for the increase in electrical voltage 124 over a value 140 prior to or subsequently to the application of the pulse sequence. It is possible to determine a time constant for the occurrence of the charge transfer in sensor element 110, in particular in cell 114, from the shape of the time characteristic of electrical voltage 124 of sensor element 110 during current pulse 130 by using an electrical capacitor to perform an analogy of a response of the cell. For this case, the time constant corresponds to the product of the value of the internal resistance and the capacitance of sensor element 110, as explained above. The value of the capacitance of sensor element 110, in particular of cell 114, may be hereby determined by an approximation, from which polarization-induced portion 138 of the increase in electrical voltage 124 may be determined during current pulse 130. The internal resistance of sensor element 110 is ultimately derived by subtracting polarization-induced portion 138 from the total increase in electrical voltage 124 from which the ohmic portion 136 sought for the internal resistance of sensor element 110 may be determined.

What is claimed is:

1. A method for determining an internal resistance of a sensor element for ascertaining a proportion of a gas component from a gas mixture in a measuring gas chamber, the method comprising:
    a) applying a current pulse to the sensor element, the current pulse inducing a charge transfer in the sensor element, the occurrence of the charge transfer causing an increase in the electrical voltage between a first electrode and a second electrode, the sensor element including at least one cell, the cell having at least the first electrode, at least the second electrode, and at least one solid electrolyte that connects the at least one first electrode and the at least one second electrode, an electrical voltage being present between the first electrode and the second electrode;
    b) ascertaining a value for the increase in the electrical voltage between the first electrode and the second electrode, wherein b) is performed at least twice at different points in time during the occurrence of the charge transfer, and a value for increasing the electrical voltage is ascertained therefrom at the different points in time; and
    c) determining the internal resistance of the sensor element from the values for increasing the electrical voltage that are ascertained at the different points in time during the occurrence of the charge transfer;
    wherein a time constant for the occurrence of the charge transfer in the sensor element is determined from the values for increasing the electrical voltage ascertained at the different points in time during the occurrence of the charge transfer; and
    wherein a time duration of the current pulse applied to the sensor element is adjusted to exceed a length of the time constant determined for the occurrence of the charge transfer in the sensor element, and wherein the current pulse is followed by a counter pulse.

2. The method as recited in claim 1, wherein a polarization-induced portion of the increase in the electrical voltage is determined from the values for increasing the electrical voltage ascertained at the different points in time during the occurrence of the charge transfer; the internal resistance of the sensor element being determined by subtracting the polarization-induced portion of the increase in the electrical voltage from the ascertained values for increasing the electrical voltage.

3. The method as recited in claim 1, wherein the time constant for the charge transfer in the sensor element is determined in a time period during which other factors that influence the electrical voltage between the first electrode and the second electrode are disregarded or ruled out.

4. The method as recited in claim 1, wherein the time constant ascertained for the occurrence of the charge transfer in the sensor element is stored in an electronic storage medium and is used for at least one subsequent determination of the internal resistance of the sensor element.

5. The method as recited in claim 1, wherein the sensor element is connected via a low-pass filter to a control unit, the low-pass filter having a corresponding time constant, a first point in time for determining a first value for increasing the electrical voltage being selected to allow the first point in time to correspond to at least three times the time constant of the low-pass filter.

6. The method as recited in claim 1, wherein the sensor element is connected via a low-pass filter to a control unit, the low-pass filter having a corresponding time constant, a first point in time for determining a first value for increasing the electrical voltage being selected to allow the first point in time to correspond to at least five times the time constant of the low-pass filter.

7. A non-transitory electronic storage medium, which stores a computer program, which is executable by a processor, comprising:
    a program code arrangement having program code for determining an internal resistance of a sensor element for ascertaining a proportion of a gas component from a gas mixture in a measuring gas chamber, the sensor element including at least one cell, the cell having at least one first electrode, at least one second electrode, and at least one solid electrolyte that connects the at least one first electrode and the at least one second electrode, an electrical voltage being present between the first electrode and the second electrode, by performing the following:
        a) applying a current pulse to the sensor element, the current pulse inducing a charge transfer in the sensor element, the occurrence of the charge transfer causing an increase in the electrical voltage between the first electrode and the second electrode;

b) ascertaining a value for the increase in the electrical voltage between the first electrode and the second electrode, wherein b) is performed at least twice at different points in time during the occurrence of the charge transfer, and a value for increasing the electrical voltage is ascertained therefrom at the different points in time; and c) determining the internal resistance of the sensor element from the values for increasing the electrical voltage that are ascertained at the different points in time during the occurrence of the charge transfer;

wherein a time constant for the occurrence of the charge transfer in the sensor element is determined from the values for increasing the electrical voltage ascertained at the different points in time during the occurrence of the charge transfer; and wherein a time duration of the current pulse applied to the sensor element is adjusted to exceed a length of the time constant determined for the occurrence of the charge transfer in the sensor element, and wherein the current pulse is followed by a counter pulse.

8. A non-transitory electronic storage medium, which stores a computer program, which is executable by a processor, comprising:

a program code arrangement having program code for determining an internal resistance of a sensor element for ascertaining a proportion of a gas component from a gas mixture in a measuring gas chamber, the sensor element including at least one cell, the cell having at least one first electrode, at least one second electrode, and at least one solid electrolyte that connects the at least one first electrode and the at least one second electrode, an electrical voltage being present between the first electrode and the second electrode, by performing the following:

a) applying a current pulse to the sensor element, the current pulse inducing a charge transfer in the sensor element, the occurrence of the charge transfer causing an increase in the electrical voltage between the first electrode and the second electrode;

b) ascertaining a value for the increase in the electrical voltage between the first electrode and the second electrode, wherein b) is performed at least twice at different points in time during the occurrence of the charge transfer, and a value for increasing the electrical voltage is ascertained therefrom at the different points in time; and c) determining the internal resistance of the sensor element from the values for increasing the electrical voltage that are ascertained at the different points in time during the occurrence of the charge transfer;

wherein a time constant for the occurrence of the charge transfer in the sensor element is determined from the values for increasing the electrical voltage ascertained at the different points in time during the occurrence of the charge transfer;

wherein the time constant for the occurrence of a charge transfer in a sensor element is stored, and wherein a time duration of the current pulse applied to the sensor element is adjusted to exceed a length of the time constant determined for the occurrence of the charge transfer in the sensor element, and wherein the current pulse is followed by a counter pulse.

9. A control unit, comprising:

an electronic storage medium, which stores a computer program, which is executable by a processor, including a program code arrangement having program code for determining an internal resistance of a sensor element for ascertaining a proportion of a gas component from a gas mixture in a measuring gas chamber, the sensor element including at least one cell, the cell having at least one first electrode, at least one second electrode, and at least one solid electrolyte that connects the at least one first electrode and the at least one second electrode, an electrical voltage being present between the first electrode and the second electrode, by performing the following:

a) applying a current pulse to the sensor element, the current pulse inducing a charge transfer in the sensor element, the occurrence of the charge transfer causing an increase in the electrical voltage between the first electrode and the second electrode;

b) ascertaining a value for the increase in the electrical voltage between the first electrode and the second electrode, wherein b) is performed at least twice at different points in time during the occurrence of the charge transfer, and a value for increasing the electrical voltage is ascertained therefrom at the different points in time; and c) determining the internal resistance of the sensor element from the values for increasing the electrical voltage that are ascertained at the different points in time during the occurrence of the charge transfer;

wherein a time constant for the occurrence of the charge transfer in the sensor element is determined from the values for increasing the electrical voltage ascertained at the different points in time during the occurrence of the charge transfer; and wherein a time duration of the current pulse applied to the sensor element is adjusted to exceed a length of the time constant determined for the occurrence of the charge transfer in the sensor element, and wherein the current pulse is followed by a counter pulse.

10. A device for ascertaining a proportion of a gas component from a gas mixture in a measuring gas chamber, comprising:

a sensor element having at least one cell, the cell having at least one first electrode, at least one second electrode, and at least one solid electrolyte that connects the at least one first electrode and the at least second electrode, an electrical voltage being present between the first electrode and the second electrode; and a control unit control unit that includes an electronic storage medium, which stores a computer program, which is executable by a processor, including a program code arrangement having program code for determining an internal resistance of the sensor element, by performing the following:

a) applying a current pulse to the sensor element, the current pulse inducing a charge transfer in the sensor element, the occurrence of the charge transfer causing an increase in the electrical voltage between the first electrode and the second electrode;

b) ascertaining a value for the increase in the electrical voltage between the first electrode and the second electrode, wherein b) is performed at least twice at different points in time during the occurrence of the charge transfer, and a value for increasing the electrical voltage is ascertained therefrom at the different points in time; and c) determining the internal resistance of the sensor element from the values for increasing the electrical voltage that are ascertained at the different points in time during the occurrence of the charge transfer;

wherein a time constant for the occurrence of the charge transfer in the sensor element is determined from the values for increasing the electrical voltage ascertained at the different points in time during the occurrence of the charge transfer; and wherein a time duration of the current pulse applied to the sensor element is adjusted to exceed a length of the time constant determined for the occurrence of the charge transfer in the sensor element, and wherein the current pulse is followed by a counter pulse.

* * * * *